000

United States Patent
Seo et al.

(10) Patent No.: US 8,980,582 B2
(45) Date of Patent: *Mar. 17, 2015

(54) BMP-6 ANTIBODIES AND DNA ENCODING THE SAME

(71) Applicant: Eli Lilly and Company, Indianapolis, IN (US)

(72) Inventors: Neungseon Steven Seo, Carmel, IN (US); Stephanie Marie Eaton Truhlar, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/316,137

(22) Filed: Jun. 26, 2014

(65) Prior Publication Data

US 2014/0309404 A1    Oct. 16, 2014

Related U.S. Application Data

(63) Continuation of application No. 14/097,335, filed on Dec. 5, 2013, now Pat. No. 8,795,665.

(60) Provisional application No. 61/737,859, filed on Dec. 17, 2012.

(51) Int. Cl.
| | |
|---|---|
| *C12N 15/00* | (2006.01) |
| *C12N 15/09* | (2006.01) |
| *C12N 15/11* | (2006.01) |
| *C12N 15/13* | (2006.01) |
| *C12N 5/07* | (2010.01) |
| *C12N 5/10* | (2006.01) |
| *C12N 5/16* | (2006.01) |
| *C12N 5/22* | (2006.01) |
| *C07K 16/22* | (2006.01) |
| *A61K 39/00* | (2006.01) |

(52) U.S. Cl.
CPC ............ *C07K 16/22* (2013.01); *A61K 2039/505* (2013.01); *A61K 2039/54* (2013.01); *A61K 2039/545* (2013.01); *C07K 2317/33* (2013.01); *C07K 2317/76* (2013.01); *C07K 2317/92* (2013.01); *C07K 2317/94* (2013.01)
USPC .......... 435/69.1; 435/326; 435/328; 435/331; 435/335; 435/336; 536/23.1

(58) Field of Classification Search
None
See application file for complete search history.

(56) References Cited

U.S. PATENT DOCUMENTS

| | | |
|---|---|---|
| 8,318,167 B2 | 11/2012 | Lin et al. |
| 8,795,665 B2 * | 8/2014 | Seo et al. .................. 424/141.1 |
| 2010/0136015 A1 | 6/2010 | Lin et al. |
| 2011/0070242 A1 | 3/2011 | Roth et al. |
| 2014/0030272 A1 | 1/2014 | Roth |
| 2014/0170161 A1 | 6/2014 | Seo et al. |

OTHER PUBLICATIONS

Kautz L., et. al., Jun. 6, 2008, Blood, vol. 112, No. 8, pp. 1503-1509.
Meynard D., et. al., Apr. 2009, Nature Genetics, vol. 41, No. 4, pp. 478-481.
Andriopoulos B., et. al., Apr. 2009, Natural Genetics, vol. 41, No. 4, pp. 482-487.
Babitt JL., et. al., Jul. 2007, Journal of Clin Invest, vol. 117, No. 7, pp. 1933-1939.
Xia Y., et. al., Mar. 7, 2008, Blood, vol. 111, No. 10, pp. 5195-5204.
De Falco, L., et al., 2013, Haematologica, 98 (6), pp. 845-853.
Yin, H., et al., Aug. 27, 2013, Arthritis Rheum., doi: 10.1002/art. 38123. [Epub ahead of print].

* cited by examiner

*Primary Examiner* — Elizabeth C Kemmerer
(74) *Attorney, Agent, or Firm* — Robert B. Johnson

(57) ABSTRACT

The present invention relates to antibodies, or antigen-binding fragments thereof, that bind to human BMP-6, compositions comprising such antibodies, or antigen-binding fragments thereof, and methods of using the same for treatment of anemia of chronic disease.

10 Claims, No Drawings

SEQUENCE LISTING

```
<160> NUMBER OF SEQ ID NOS: 17

<210> SEQ ID NO 1
<211> LENGTH: 490
<212> TYPE: PRT
<213> ORGANISM: Homo sapiens

<400> SEQUENCE: 1

Pro Pro Pro Leu Arg Pro Pro Leu Pro Ala Ala Ala Ala Ala Ala
1               5                  10                  15

Gly Gly Gln Leu Leu Gly Asp Gly Gly Ser Pro Gly Arg Thr Glu Gln
                20                  25                  30

Pro Pro Pro Ser Pro Gln Ser Ser Ser Gly Phe Leu Tyr Arg Arg Leu
                35                  40                  45

Lys Thr Gln Glu Lys Arg Glu Met Gln Lys Glu Ile Leu Ser Val Leu
    50                  55                  60

Gly Leu Pro His Arg Pro Arg Pro Leu His Gly Leu Gln Gln Pro Gln
65                  70                  75                  80

Pro Pro Ala Leu Arg Gln Gln Glu Glu Gln Gln Gln Gln Gln Gln Leu
                85                  90                  95

Pro Arg Gly Glu Pro Pro Pro Gly Arg Leu Lys Ser Ala Pro Leu Phe
                100                 105                 110

Met Leu Asp Leu Tyr Asn Ala Leu Ser Ala Asp Asn Glu Asp Gly
                115                 120                 125

Ala Ser Glu Gly Glu Arg Gln Gln Ser Trp Pro His Glu Ala Ala Ser
    130                 135                 140

Ser Ser Gln Arg Arg Gln Pro Pro Pro Gly Ala Ala His Pro Leu Asn
145                 150                 155                 160

Arg Lys Ser Leu Leu Ala Pro Gly Ser Gly Ser Gly Gly Ala Ser Pro
                165                 170                 175

Leu Thr Ser Ala Gln Asp Ser Ala Phe Leu Asn Asp Ala Asp Met Val
                180                 185                 190

Met Ser Phe Val Asn Leu Val Glu Tyr Asp Lys Glu Phe Ser Pro Arg
                195                 200                 205

Gln Arg His His Lys Glu Phe Lys Phe Asn Leu Ser Gln Ile Pro Glu
    210                 215                 220

Gly Glu Val Val Thr Ala Ala Glu Phe Arg Ile Tyr Lys Asp Cys Val
225                 230                 235                 240

Met Gly Ser Phe Lys Asn Gln Thr Phe Leu Ile Ser Ile Tyr Gln Val
                245                 250                 255

Leu Gln Glu His Gln His Arg Asp Ser Asp Leu Phe Leu Leu Asp Thr
                260                 265                 270

Arg Val Val Trp Ala Ser Glu Glu Gly Trp Leu Glu Phe Asp Ile Thr
                275                 280                 285

Ala Thr Ser Asn Leu Trp Val Val Thr Pro Gln His Asn Met Gly Leu
                290                 295                 300
```

```
Gln Leu Ser Val Val Thr Arg Asp Gly Val His Val His Pro Arg Ala
305                 310                 315                 320

Ala Gly Leu Val Gly Arg Asp Gly Pro Tyr Asp Lys Gln Pro Phe Met
            325                 330                 335

Val Ala Phe Phe Lys Val Ser Glu Val His Val Arg Thr Thr Arg Ser
        340                 345                 350

Ala Ser Ser Arg Arg Arg Gln Gln Ser Arg Asn Arg Ser Thr Gln Ser
            355                 360                 365

Gln Asp Val Ala Arg Val Ser Ser Ala Ser Asp Tyr Asn Ser Ser Glu
        370                 375                 380

Leu Lys Thr Ala Cys Arg Lys His Glu Leu Tyr Val Ser Phe Gln Asp
385                 390                 395                 400

Leu Gly Trp Gln Asp Trp Ile Ile Ala Pro Lys Gly Tyr Ala Ala Asn
            405                 410                 415

Tyr Cys Asp Gly Glu Cys Ser Phe Pro Leu Asn Ala His Met Asn Ala
        420                 425                 430

Thr Asn His Ala Ile Val Gln Thr Leu Val His Leu Met Asn Pro Glu
        435                 440                 445

Tyr Val Pro Lys Pro Cys Cys Ala Pro Thr Lys Leu Asn Ala Ile Ser
450                 455                 460

Val Leu Tyr Phe Asp Asp Asn Ser Asn Val Ile Leu Lys Lys Tyr Arg
465                 470                 475                 480

Asn Met Val Val Arg Ala Cys Gly Cys His
            485                 490
```

```
<210> SEQ ID NO 2
<211> LENGTH: 11
<212> TYPE: PRT
<213> ORGANISM: Artificial Sequence
<220> FEATURE:
<223> OTHER INFORMATION: Synthetic construct

<400> SEQUENCE: 2

Arg Ser Ser Glu Asn Ile Tyr Arg Asn Leu Ala
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic construct

<400> SEQUENCE: 3

Ala Ala Thr Asn Leu Ala Asp
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic construct

<400> SEQUENCE: 4

Gln Gly Ile Trp Gly Thr Pro Leu Thr
1               5

<210> SEQ ID NO 5
<211> LENGTH: 10
```

<210> SEQ ID NO 5
<211> LENGTH: (not shown)
<212> TYPE: PRT
<213> ORGANISM: Artificial Sequence
<220> FEATURE:
<223> OTHER INFORMATION: Synthetic construct

<400> SEQUENCE: 5

```
Gly Tyr Thr Phe Thr Ser Tyr Ala Met His
1               5                   10
```

<210> SEQ ID NO 6
<211> LENGTH: 17
<212> TYPE: PRT
<213> ORGANISM: Artificial Sequence
<220> FEATURE:
<223> OTHER INFORMATION: Synthetic construct

<400> SEQUENCE: 6

```
Tyr Ile Asn Pro Tyr Asn Asp Gly Thr Lys Tyr Asn Glu Asn Phe Lys
1               5                   10                  15

Gly
```

<210> SEQ ID NO 7
<211> LENGTH: 17
<212> TYPE: PRT
<213> ORGANISM: Artificial Sequence
<220> FEATURE:
<223> OTHER INFORMATION: Synthetic construct

<400> SEQUENCE: 7

```
Tyr Ile Asn Pro Tyr Asn Arg Gly Thr Lys Tyr Asn Glu Asn Phe Lys
1               5                   10                  15

Gly
```

<210> SEQ ID NO 8
<211> LENGTH: 9
<212> TYPE: PRT
<213> ORGANISM: Artificial Sequence
<220> FEATURE:
<223> OTHER INFORMATION: Synthetic construct

<400> SEQUENCE: 8

```
Arg Pro Phe Gly Asn Ala Met Asp Ile
1               5
```

<210> SEQ ID NO 9
<211> LENGTH: 107
<212> TYPE: PRT
<213> ORGANISM: Artificial Sequence
<220> FEATURE:
<223> OTHER INFORMATION: Synthetic construct

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Asn Ile Tyr Arg Asn
                20                  25                  30

Leu Ala Trp Tyr Gln Gln Lys Pro Gly Lys Ala Pro Lys Leu Leu Ile
            35                  40                  45

Tyr Ala Ala Thr Asn Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ile Trp Gly Thr Pro Leu
```

```
                    85                  90                  95

Thr Phe Gly Gly Gly Thr Lys Val Glu Ile Lys
            100                 105

<210> SEQ ID NO 10
<211> LENGTH: 118
<212> TYPE: PRT
<213> ORGANISM: Artificial Sequence
<220> FEATURE:
<223> OTHER INFORMATION: Synthetic construct

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
            100                 105                 110

Leu Val Thr Val Ser Ser
        115

<210> SEQ ID NO 11
<211> LENGTH: 118
<212> TYPE: PRT
<213> ORGANISM: Artificial Sequence
<220> FEATURE:
<223> OTHER INFORMATION: Synthetic construct

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Tyr Ile Asn Pro Tyr Asn Arg Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
            100                 105                 110

Leu Val Thr Val Ser Ser
        115

<210> SEQ ID NO 12
<211> LENGTH: 214
<212> TYPE: PRT
<213> ORGANISM: Artificial Sequence
<220> FEATURE:
```

<223> OTHER INFORMATION: Synthetic construct

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Asn Ile Tyr Arg Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ile Trp Gly Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 444
<212> TYPE: PRT
<213> ORGANISM: Artificial Sequence
<220> FEATURE:
<223> OTHER INFORMATION: Synthetic construct

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 14
<211> LENGTH: 444
<212> TYPE: PRT
<213> ORGANISM: Artificial Sequence
<220> FEATURE:
<223> OTHER INFORMATION: Synthetic construct

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

```
Gly Tyr Ile Asn Pro Tyr Asn Arg Gly Thr Lys Tyr Asn Glu Asn Phe
         50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Pro Phe Gly Asn Ala Met Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 15
<211> LENGTH: 642
```

<212> TYPE: DNA
<213> ORGANISM: Artificial Sequence
<220> FEATURE:
<223> OTHER INFORMATION: Synthetic construct

<400> SEQUENCE: 15

| | | | | | |
|---|---|---|---|---|---|
| gacatccaga | tgacccagtc | tccatcctcc | ctgtctgcat | ctgtaggaga | cagagtcacc | 60 |
| atcacttgcc | gatcttccga | aaatatttac | cgtaatttag | catggtatca | gcagaaacca | 120 |
| gggaaagccc | ctaagctcct | gatctatgct | gcaacaaact | tagcagatgg | ggtcccatca | 180 |
| aggttcagtg | gcagtggatc | tgggacagat | ttcactctca | ccatcagcag | tctgcaacct | 240 |
| gaagattttg | caacttacta | ctgtcaaggc | atttgggta | ctccgctcac | tttcggcgga | 300 |
| gggaccaagg | tggagatcaa | acgaactgtg | gctgcaccat | ctgtcttcat | cttcccgcca | 360 |
| tctgatgagc | agttgaaatc | tggaactgcc | tctgttgtgt | gcctgctgaa | taacttctat | 420 |
| cccagagagg | ccaaagtaca | gtggaaggtg | gataacgccc | tccaatcggg | taactcccag | 480 |
| gagagtgtca | cagagcagga | cagcaaggac | agcacctaca | gcctcagcag | caccctgacg | 540 |
| ctgagcaaag | cagactacga | gaaacacaaa | gtctacgcct | gcgaagtcac | ccatcagggc | 600 |
| ctgagctcgc | ccgtcacaaa | gagcttcaac | aggggagagt | gc | | 642 |

<210> SEQ ID NO 16
<211> LENGTH: 1332
<212> TYPE: DNA
<213> ORGANISM: Artificial Sequence
<220> FEATURE:
<223> OTHER INFORMATION: Synthetic construct

<400> SEQUENCE: 16

| | | | | | |
|---|---|---|---|---|---|
| caggtgcagc | tggtgcagtc | tggggctgag | gtgaagaagc | ctgggtcctc | ggtgaaggtc | 60 |
| tcctgcaagg | cttctggata | cacattcact | agctatgcta | tgcactgggt | gcgacaggcc | 120 |
| cctggacaag | ggcttgagtg | gatgggatat | attaatcctt | ataatgatgg | tactaagtac | 180 |
| aatgagaact | tcaaaggcag | agtcacgatt | accgcggacg | aatccacgag | cacagcctac | 240 |
| atggagctga | gcagcctgag | atctgaggac | acggccgtgt | attactgtgc | gagaaggccc | 300 |
| tttggtaacg | ctatggacat | ttggggccag | ggcaccctgg | tcaccgtctc | ctcagcctcc | 360 |
| accaagggcc | catcggtctt | cccgctagcg | ccctgctcca | ggagcacctc | cgagagcaca | 420 |
| gccgccctgg | gctgcctggt | caaggactac | ttccccgaac | cggtgacggt | gtcgtggaac | 480 |
| tcaggcgccc | tgaccagcgg | cgtgcacacc | ttcccggctg | tcctacagtc | ctcaggactc | 540 |
| tactccctca | gcagcgtggt | gaccgtgccc | tccagcagct | gggcacgaa | gacctacacc | 600 |
| tgcaacgtag | atcacaagcc | cagcaacacc | aaggtggaca | agagagttga | gtccaaatat | 660 |
| ggtccccat | gcccaccctg | cccagcacct | gaggccgccg | ggggaccatc | agtcttcctg | 720 |
| ttccccccaa | aacccaagga | cactctcatg | atctcccgga | cccctgaggt | cacgtgcgtg | 780 |
| gtggtggacg | tgagccagga | agaccccgag | gtccagttca | actggtacgt | ggatggcgtg | 840 |
| gaggtgcata | atgccaagac | aaagccgcgg | gaggagcagt | tcaacagcac | gtaccgtgtg | 900 |
| gtcagcgtcc | tcaccgtcct | gcaccaggac | tggctgaacg | gcaaggagta | caagtgcaag | 960 |
| gtctccaaca | aaggcctccc | gtcctccatc | gagaaaacca | tctccaaagc | caaagggcag | 1020 |
| ccccgagagc | cacaggtgta | caccctgccc | ccatcccagg | aggagatgac | caagaaccag | 1080 |
| gtcagcctga | cctgcctggt | caaaggcttc | taccccagcg | acatcgccgt | ggagtgggaa | 1140 |

-continued

```
agcaatgggc agccggagaa caactacaag accacgcctc ccgtgctgga ctccgacggc    1200
tccttcttcc tctacagcag gctaaccgtg acaagagca ggtggcagga ggggaatgtc    1260
ttctcatgct ccgtgatgca tgaggctctg cacaaccact acacacagaa gagcctctcc    1320
ctgtctctgg gt                                                        1332

<210> SEQ ID NO 17
<211> LENGTH: 1332
<212> TYPE: DNA
<213> ORGANISM: Artificial Sequence
<220> FEATURE:
<223> OTHER INFORMATION: Synthetic construct

<400> SEQUENCE: 17
caggtgcagc tggtgcagtc tggggctgag gtgaagaagc ctgggtcctc ggtgaaggtc      60
tcctgcaagg cttctggata tacattcact agctatgcta tgcactgggt gcgacaggcc    120
cctggacaag gcttgagtg gatgggatat attaatcctt ataatcgtgg tactaagtac     180
aatgagaact tcaaaggcag agtcacgatt accgcggacg aatccacgag cacagcctac    240
atggagctga gcagcctgag atctgaggac acggccgtgt attactgtgc gagaaggccc    300
tttggtaacg ctatggacat ttggggccag ggcaccctgg tcaccgtctc ctcagcctcc    360
accaagggcc catcggtctt cccgctagcg ccctgctcca ggagcacctc cgagagcaca    420
gccgccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcacgaa gacctacacc     600 tgcaacgtag atcacaagcc cagcaacacc aaggtggaca gagagttga gtccaaatat     660 ggtcccccat gcccaccctg cccagcacct gaggccgccg ggggaccatc agtcttcctg    720
ttccccccaa aacccaagga cactctcatg atctcccgga cccctgaggt cacgtgcgtg    780
gtggtggacg tgagccagga agaccccgag gtccagttca actggtacgt ggatggcgtg    840
gaggtgcata tgccaagac aaagccgcgg gaggagcagt tcaacagcac gtaccgtgtg     900
gtcagcgtcc tcaccgtcct gcaccaggac tggctgaacg gcaaggagta caagtgcaag    960
gtctccaaca aaggcctccc gtcctccatc gagaaaacca tctccaaagc caaagggcag    1020
ccccgagagc cacaggtgta caccctgccc ccatcccagg aggagatgac caagaaccag    1080
gtcagcctga cctgcctggt caaaggcttc taccccagcg acatcgccgt ggagtgggaa    1140
agcaatgggc agccggagaa caactacaag accacgcctc ccgtgctgga ctccgacggc    1200
tccttcttcc tctacagcag gctaaccgtg acaagagca ggtggcagga ggggaatgtc    1260
ttctcatgct ccgtgatgca tgaggctctg cacaaccact acacacagaa gagcctctcc    1320
ctgtctctgg gt                                                       1332
```

BMP-6 ANTIBODIES AND DNA ENCODING THE SAME

The present invention relates to the field of medicine. More particularly, the present invention relates to antibodies, or antigen-binding fragments thereof, that bind human BMP-6 and may be useful for treating anemia of chronic disease (ACD), such as anemia of cancer, or anemia of chronic kidney disease (CKD).

BMP-6 is a member of the bone morphogenetic protein (BMP) family; there are more than twenty members in the BMP family. BMP family members are ligands that initiate signaling in the SMAD pathway leading to transcriptional modulation in the cell. BMP-6 knock-out mice are reported to be viable and fertile, and show normal bone and cartilage development, while knock-out mice for the closely related BMP-7 die after birth with kidney, eye, and bone defects. Individual knock-outs of either BMP-6 or BMP-7 have been shown to not alter cardiogenesis, but the double knock-out of BMP-6 and BMP-7 did demonstrate several defects and delays in the heart, and the embryos died due to cardiac insufficiency. The presence of BMP-7 has also been shown in mouse models to be important in preventing progression of chronic heart disease associated with fibrosis. Therefore, when inhibiting human BMP-6 with a BMP-6 antibody, cross-reactivity against BMP-7 is likely not desirable.

Certain chronic diseases, such as cancer, kidney disease, and autoimmune disorders, can lead to ACD when overactive inflammatory cytokines cause dysregulation of iron homeostasis, reduction of erythropoiesis, and a decrease in the life span of red blood cells. Hepcidin has been identified as a key hormone involved in iron homeostasis; high levels of hepcidin have been associated with the iron restricted erythropoiesis seen in ACD. BMP-6 has been shown to increase hepcidin expression.

WO 2010/056981 disclosed administration in mice of a mouse antibody generated to human BMP-6; a decrease in hepcidin and an increase in iron was reported at one time point after a three day regimen with this mouse antibody, MAB507, that was commercially available from R&D Systems. Selectivity towards BMPs was also disclosed, and it was shown that administration of the BMP-6 antibody MAB507 inhibited BMP-7 at certain doses. However, to date, no antibody targeting BMP-6 has been approved for therapeutic use.

There remains a need to provide alternative BMP-6 antibodies. In particular, there remains a need to provide potent BMP-6 antibodies that are selective for BMP-6 over other BMP family members, including BMP-7. There also remains a need to provide potent BMP-6 antibodies that are selective for BMP-6 over other BMP family members, including BMP-7, and produce a prolonged pharmacodynamic response. There also remains a need to provide potent BMP-6 antibodies that are selective for BMP-6 over other BMP family members, including BMP-7, for the treatment of ACD.

Accordingly, the present invention provides an antibody, or antigen-binding fragment thereof, that binds to human BMP-6 (SEQ ID NO: 1), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of RSSENIYRNLA (SEQ ID NO: 2), the LCDR2 is the polypeptide of AATNLAD (SEQ ID NO: 3), the LCDR3 is the polypeptide of QGIWGTPLT (SEQ ID NO: 4), the HCDR1 is the polypeptide of GYTFTSYAMH (SEQ ID NO: 5), the HCDR2 is the polypeptide of YINPYNDGTKYNENFKG (SEQ ID NO: 6) or YINPYNRGTKYNENFKG (SEQ ID NO: 7), and the HCDR3 is the polypeptide of RPFGNAMDI (SEQ ID NO: 8).

In an embodiment, the present invention provides an antibody, or antigen-binding fragment thereof, that binds to human BMP-6 (SEQ ID NO: 1), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of RSSENIYRNLA (SEQ ID NO: 2), the LCDR2 is the polypeptide of AATNLAD (SEQ ID NO: 3), the LCDR3 is the polypeptide of QGIWGTPLT (SEQ ID NO: 4), the HCDR1 is the polypeptide of GYTFTSYAMH (SEQ ID NO: 5), the HCDR2 is the polypeptide of YINPYNDGTKYNENFKG (SEQ ID NO: 6), and the HCDR3 is the polypeptide of RPFGNAMDI (SEQ ID NO: 8).

In an embodiment, the present invention provides an antibody, or antigen-binding fragment thereof, that binds to human BMP-6 (SEQ ID NO: 1), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of RSSENIYRNLA (SEQ ID NO: 2), the LCDR2 is the polypeptide of AATNLAD (SEQ ID NO: 3), the LCDR3 is the polypeptide of QGIWGTPLT (SEQ ID NO: 4), the HCDR1 is the polypeptide of GYTFTSYAMH (SEQ ID NO: 5), the HCDR2 is the polypeptide of YINPYNRGTKYNENFKG (SEQ ID NO: 7), and the HCDR3 is the polypeptide of RPFGNAMDI (SEQ ID NO: 8).

In an embodiment, the present invention provides an antibody, or antigen-binding fragment thereof, that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10 or SEQ ID NO: 11. In a further embodiment, the present invention provides an antibody, or antigen-binding fragment thereof, that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10. In another embodiment, the present invention provides an antibody, or antigen-binding fragment thereof, that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 11.

In an embodiment, the present invention provides an antibody that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10 or SEQ ID NO: 11. In a further embodiment, the present invention provides an antibody that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 10. In another embodiment, the present invention provides an antibody that binds to human BMP-6 (SEQ ID NO: 1), comprising an LCVR and an HCVR, wherein the LCVR is the polypeptide of SEQ ID NO: 9, and the HCVR is the polypeptide of SEQ ID NO: 11.

In an embodiment, the present invention provides an antibody that binds to human BMP-6 (SEQ ID NO: 1), comprising a light chain (LC) and a heavy chain (HC), wherein the LC is the polypeptide of SEQ ID NO: 12, and the HC is the polypeptide of SEQ ID NO: 13 or SEQ ID NO: 14. In a further embodiment, the present invention provides an antibody that binds to human BMP-6 (SEQ ID NO: 1), comprising a LC and a HC, wherein the LC is the polypeptide of SEQ ID NO: 12, and the HC is the polypeptide of SEQ ID NO: 13. In another embodiment, the present invention provides an antibody that binds to human BMP-6 (SEQ ID NO: 1), comprising a LC and a HC, wherein the LC is the polypeptide of SEQ ID NO: 12, and the HC is the polypeptide of SEQ ID NO: 14.

In an embodiment, the present invention provides an antibody that binds to human BMP-6 (SEQ ID NO: 1), comprising two light chains and two heavy chains, wherein each light chain is the polypeptide of SEQ ID NO: 12, and each heavy chain is the polypeptide of SEQ ID NO: 13. In an embodiment, the present invention provides an antibody that binds to human BMP-6 (SEQ ID NO: 1), comprising two light chains and two heavy chains, wherein each light chain is the polypeptide of SEQ ID NO: 12, and each heavy chain is the polypeptide of SEQ ID NO: 14.

The present invention also relates to polynucleotides encoding the above-described antibodies, or antigen-binding fragments thereof, of the present invention that may be in the form of RNA or in the form of DNA, which DNA includes cDNA, and synthetic DNA. The DNA may be double-stranded or single-stranded. The coding sequences that encode the antibody, or antigen-binding fragment thereof, of the present invention may vary as a result of the redundancy or degeneracy of the genetic code.

In an embodiment, the present invention provides a DNA molecule comprising a polynucleotide sequence encoding a heavy chain polypeptide having the amino acid sequence of SEQ ID NO: 13 or the amino acid sequence of SEQ ID NO: 14. In an embodiment, the present invention provides a DNA molecule comprising a polynucleotide sequence encoding a light chain polypeptide having the amino acid sequence of SEQ ID NO: 12.

In an embodiment, the present invention provides a DNA molecule comprising a polynucleotide sequence encoding a heavy chain polypeptide having the amino acid sequence of SEQ ID NO: 13 and comprising a polynucleotide sequence encoding a light chain polypeptide having the amino acid sequence of SEQ ID NO: 12. In an embodiment, the present invention provides a DNA molecule comprising a polynucleotide sequence encoding a heavy chain polypeptide having the amino acid sequence of SEQ ID NO: 14 and comprising a polynucleotide sequence encoding a light chain polypeptide having the amino acid sequence of SEQ ID NO: 12.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibody, or antigen-binding fragment thereof, of the present invention may readily be produced in mammalian cells such as CHO, NS0, HEK293 or COS cells; in bacterial cells such as *E. coli, Bacillus subtilis,* or *Pseudomonas fluorescence;* or in fungal or yeast cells. The host cells are cultured using techniques well known in the art.

The vectors containing the polynucleotide sequences of interest (e.g., the polypeptides of the antibody, or antigen-binding fragment thereof, and expression control sequences) can be transferred into the host cell by well-known methods, which vary depending on the type of cellular host. For example, calcium chloride transformation is commonly utilized for prokaryotic cells, whereas calcium phosphate treatment or electroporation may be used for other cellular hosts.

In an embodiment, the present invention provides a mammalian cell comprising a DNA molecule or molecules of the present invention, which cell is capable of expressing an antibody comprising a heavy chain having the amino acid sequence of SEQ ID NO: 13 and a light chain having the amino acid sequence of SEQ ID NO: 12. In an embodiment, the present invention provides a mammalian cell comprising DNA molecules of the present invention, which cell is capable of expressing an antibody comprising a heavy chain having the amino acid sequence of SEQ ID NO: 14 and a light chain having the amino acid sequence of SEQ ID NO: 12.

In an embodiment, the present invention provides a process for producing an antibody of the present invention comprising a heavy chain whose amino acid sequence is SEQ ID NO: 13 and a light chain whose amino acid sequence is SEQ ID NO: 12, comprising cultivating a mammalian cell of the present invention under conditions such that the antibody is expressed, and recovering the expressed antibody. In an embodiment, the present invention provides a process for producing an antibody of the present invention comprising a heavy chain whose amino acid sequence is SEQ ID NO: 14 and a light chain whose amino acid sequence is SEQ ID NO: 12, comprising cultivating a mammalian cell of the present invention under conditions such that the antibody is expressed, and recovering the expressed antibody. In a further embodiment, the present invention provides an antibody produced by a process of the present invention.

In an embodiment, the present invention provides pharmaceutical compositions comprising an antibody, or antigen-binding fragment thereof, of the present invention, and an acceptable carrier, diluent, or excipient. More particularly, the compositions of the present invention further comprise one or more additional therapeutic agents.

In an embodiment, the present invention provides a method of treating anemia, comprising administering to a patient in need thereof, an effective amount of an antibody, or antigen-binding fragment thereof, of the present invention. In a further embodiment, the present invention provides a method of treating anemia, comprising administering an effective amount of an antibody, or antigen-binding fragment thereof, of the present invention, wherein the anemia is anemia of chronic disease. In another embodiment, the present invention provides a method of treating anemia, comprising administering an effective amount of an antibody, or antigen-binding fragment thereof, of the present invention, wherein the anemia of chronic disease is selected from the group consisting of anemia of cancer, and anemia of chronic kidney disease.

In an embodiment, the present invention provides a method of treating hepcidin related iron restricted anemia, comprising administering to a patient in need thereof, an effective amount of an antibody, or antigen-binding fragment thereof, of the present invention. In a further embodiment, the present invention provides a method of treating hepcidin related iron restricted anemia, comprising administering an effective amount of an antibody, or antigen-binding fragment thereof, of the present invention, wherein the hepcidin related iron restricted anemia is selected from the group consisting of anemia of cancer, and anemia of chronic kidney disease.

In an embodiment, the present invention provides a method of treating iron refractory iron deficiency anemia (IRIDA), comprising administering to a patient in need thereof, an effective amount of an antibody, or antigen-binding fragment thereof, of the present invention. In a further embodiment, the present invention provides a method of treating IRIDA, comprising administering to a patient in need thereof, an effective amount of an antibody, or antigen-binding fragment thereof, of the present invention, wherein IRIDA is caused by a defect in the TMPRSS6 gene.

In an embodiment, the present invention provides a method of treating Sjogren's syndrome, comprising administering to a patient in need thereof, an effective amount of an antibody, or antigen-binding fragment thereof, of the present invention.

In an embodiment, the present invention provides a method of increasing serum iron levels, reticulocyte count, red blood cell count, hemoglobin, and/or hematocrit, comprising administering to a patient in need thereof, an effective amount of an antibody, or antigen-binding fragment thereof, of the present invention. In another embodiment, the present invention provides a method of increasing serum iron levels comprising administering to a patient in need thereof, an effective amount of an antibody, or antigen-binding fragment thereof, of the present invention. In another embodiment, the present invention provides a method of increasing reticulocyte count comprising administering to a patient in need thereof, an effective amount of an antibody, or antigen-binding fragment thereof, of the present invention. In another embodiment, the present invention provides a method of increasing red blood cell count comprising administering to a patient in need thereof, an effective amount of an antibody, or antigen-binding fragment thereof, of the present invention. In another embodiment, the present invention provides a method of increasing hemoglobin comprising administering to a patient in need thereof, an effective amount of an antibody, or antigen-binding fragment thereof, of the present invention. In another embodiment, the present invention provides a method of increasing hematocrit comprising administering to a patient in need thereof, an effective amount of an antibody, or antigen-binding fragment thereof, of the present invention.

In an embodiment, the present invention provides an antibody, or antigen-binding fragment thereof, of the present invention for use in therapy. In a further embodiment, the present invention provides an antibody, or antigen-binding fragment thereof, of the present invention for use in the treatment of anemia. In another embodiment, the present invention provides an antibody, or antigen-binding fragment thereof, of the present invention for use in the treatment of anemia of chronic disease. In another embodiment, the present invention provides an antibody, or antigen-binding fragment thereof, of the present invention for use in the treatment of anemia of cancer or anemia of chronic kidney disease.

In an embodiment, the present invention provides an antibody, or antigen-binding fragment thereof, of the present invention for use in the treatment of hepcidin related iron restricted anemia. In another embodiment, the present invention provides an antibody, or antigen-binding fragment thereof, of the present invention for use in the treatment of hepcidin related iron restricted anemia of cancer. In another embodiment, the present invention provides an antibody, or antigen-binding fragment thereof, of the present invention for use in the treatment of hepcidin related iron restricted anemia of chronic kidney disease.

In an embodiment, the present invention provides an antibody, or antigen-binding fragment thereof, of the present invention for use in the treatment of IRIDA. In a further embodiment, the present invention provides an antibody, or antigen-binding fragment thereof, of the present invention for use in the treatment of IRIDA, wherein IRIDA is caused by a defect in the TMPRSS6 gene.

In an embodiment, the present invention provides an antibody, or antigen-binding fragment thereof, of the present invention for use in the treatment of Sjogren's syndrome.

In an embodiment, the present invention provides the use of an antibody, or antigen-binding fragment thereof, of the present invention for the manufacture of a medicament. In a further embodiment, the present invention provides the use of an antibody, or antigen-binding fragment thereof, of the present invention for the manufacture of a medicament for the treatment of anemia. In another embodiment, the present invention provides the use of an antibody, or antigen-binding fragment thereof, of the present invention for the manufacture of a medicament for the treatment of anemia of chronic disease. In another embodiment, the present invention provides the use of an antibody, or antigen-binding fragment thereof, of the present invention for the manufacture of a medicament for the treatment of anemia of chronic kidney disease. In another embodiment, the present invention provides the use of an antibody, or antigen-binding fragment thereof, of the present invention for the manufacture of a medicament for the treatment of anemia of cancer.

In an embodiment, the present invention provides the use of an antibody, or antigen-binding fragment thereof, of the present invention for the manufacture of a medicament for the treatment of IRIDA. In a further embodiment, the present invention provides the use of an antibody, or antigen-binding fragment thereof, of the present invention for the manufacture of a medicament for the treatment of IRIDA, wherein IRIDA is caused by a defect in the TMPRSS6 gene.

In an embodiment, the present invention provides the use of an antibody, or antigen-binding fragment thereof, of the present invention for the manufacture of a medicament for the treatment of Sjogren's syndrome.

The general structure of an "antibody" is very well-known in the art. For an antibody of the IgG type, there are four amino acid chains (two "heavy" chains and two "light" chains) that are cross-linked via intra- and inter-chain disulfide bonds. For an antibody, one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain. An antigen-binding fragment is a fragment of an antibody, such as a Fab, Fab', F(ab')$_2$, single-chain variable fragment (scFv), or di-scFv.

When expressed in certain biological systems, antibodies having human Fc sequences which are glycosylated in the Fc region. Antibodies may be glycosylated at other positions as well. One of skill in the art will appreciate that antibodies of the present invention may contain such glycosylation. Typically, glycosylation occurs in the Fc region of the antibody at a highly conserved N-glycosylation site. N-glycans typically attach to asparagines. Asparagine 295, by sequential numbering, is predicted to be a glycosylation site for antibodies of the present invention.

An antibody of the present invention is an engineered antibody that has been designed to have frameworks, hinge regions, and constant regions of human origin that are identical with or substantially identical with frameworks and constant regions derived from human genomic sequences. Fully human frameworks, hinge regions, and constant regions are those human germline sequences as well as sequences with naturally-occurring somatic mutations and/or those with engineered mutations. An antibody of the present invention may comprise framework, hinge, or constant regions derived from a fully human framework, hinge, or constant region containing one or more amino acid substitutions, deletions, or additions therein. Further, an antibody of the present invention is substantially non-immunogenic in humans.

Antibody I comprises two light chains and two heavy chains, wherein each of the light chains consists of the polypeptide of SEQ ID NO: 12 and each of the heavy chains consists of the polypeptide of SEQ ID NO: 13. Antibody II comprises two light chains and two heavy chains, wherein each of the light chains consists of the polypeptide of SEQ ID NO: 12 and each of the heavy chains consists of the polypeptide of SEQ ID NO: 14. A particular DNA molecule encoding each of the heavy chains of Antibody I is SEQ ID NO: 16, and a particular DNA molecule encoding each of the light chains of Antibody I is SEQ ID NO: 15. A particular DNA molecule encoding each of the heavy chains of Antibody II is SEQ ID NO: 17, and a particular DNA molecule encoding each of the light chains of Antibody II is SEQ ID NO: 15 .

An antibody, or antigen-binding fragment thereof, of the present invention can be produced using techniques well known in the art, e.g., recombinant technologies, phage display technologies, synthetic technologies, or combinations of such technologies or other technologies readily known in the art. Methods for producing and purifying antibodies are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

Anemia of CKD is anemia that is an early and common complication in patients suffering with CKD. Anemia of cancer is anemia caused by hematological malignancies and some solid tumors; whereas, chemotherapy-induced anemia is anemia caused by the treatment of cancer patients with chemotherapeutic agents. Anemia in CKD exacerbates diabetic neuropathy, cardiovascular disease, and retinopathy, among other conditions. Cancer-related anemia is associated with an increased relative risk of death. Current treatment options for cancer-related anemia are limited to blood transfusions, as erythropoiesis-stimulating agents are only indicated for chemotherapy-induced anemia.

"Binds" as used herein in reference to the affinity of a BMP-6 antibody, or antigen-binding fragment thereof, for human BMP-6, is intended to mean, unless indicated otherwise, a $K_D$ of less than about $1 \times 10^{-8}$ M, preferably, less than about $1 \times 10^{-9}$ M as determined by common methods known in the art, including by use of a surface plasmon resonance (SPR) biosensor at 37° C. essentially as described herein. The term "selective" used herein in reference to an antibody of the present invention refers to an antibody that binds human BMP-6 with a $K_D$ about 1000-, 500-, 200-, 100-, 50-, 10-, or about 5-fold lower than the antibody binds at least one member of the BMP family, including, but not limited to, human BMP-5 or human BMP-7, as measured by surface plasmon resonance at 37° C. Additionally, or alternatively, a BMP-6 selective antibody, or antigen-binding fragment thereof, of the present invention binds human BMP-6 but does not bind or only minimally binds to at least one member of the human BMP family, including, but not limited to human BMP-5 or human BMP-7, when assayed by the methods described in Examples 2-3 herein below.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed. A patient refers to a mammal, preferably a human with a disease, disorder or condition that would benefit from inhibition of BMP-6 activity.

An antibody, or antigen-binding fragment thereof, of the present invention, or pharmaceutical composition comprising the same, may be administered by parenteral routes (e.g., subcutaneous, intravenous, intraperitoneal, intramuscular, or transdermal). An antibody, or antigen-binding fragment thereof, of the present invention may be administered to a patient alone or in combination with a pharmaceutically acceptable carrier and/or diluent in single or multiple doses. Pharmaceutical compositions of the present invention can be prepared by methods well known in the art (e.g., *Remington: The Science and Practice of Pharmacy*, $19^{th}$ ed. (1995), A. Gennaro et al., Mack Publishing Co.) and comprise an antibody, as disclosed herein, and one or more pharmaceutically acceptable carriers, diluents, or excipients.

EXAMPLE 1

Antibody Expression and Purification

The polypeptides of the variable regions of the heavy chain and light chain, the complete heavy chain and light chain amino acid sequences of Antibody I and II, and the nucleotide sequences encoding the same, are listed below in the section entitled "Amino Acid and Nucleotide Sequences." In addition, the light chain and heavy chain CDR polypeptides are shown in Table 1.

The antibodies, or antigen-binding fragments thereof, of the present invention, including, but not limited to, Antibodies I and II, can be made and purified essentially as follows. An appropriate host cell, such as HEK 293 EBNA or CHO, can be either transiently or stably transfected with an expression system for secreting antibodies using an optimal predetermined HC:LC vector ratio or a single vector system encoding both HC and LC. Clarified media, into which the antibody has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is greater than 95%. The product may be immediately frozen at –70° C. or may be lyophilized.

TABLE 1

SEQ ID NOs

| Antibody | Light Chain | Heavy Chain | LCVR | HCVR |
|---|---|---|---|---|
| I | 12 | 13 | 9 | 10 |
| II | 12 | 14 | 9 | 11 |

| Antibody | LCDR1 | LCDR2 | LCDR3 |
|---|---|---|---|
| I | RSSENIYRNLA (SEQ ID NO: 2) | AATNLAD (SEQ ID NO: 3) | QGIWGTPLT (SEQ ID NO: 4) |
| II | RSSENIYRNLA (SEQ ID NO: 2) | AATNLAD (SEQ ID NO: 3) | QGIWGTPLT (SEQ ID NO: 4) |

| Antibody | HCDR1 | HCDR2 | HCDR3 |
|---|---|---|---|
| I | GYTFTSYAMH (SEQ ID NO: 5) | YINPYNDGTKYNENFKG (SEQ ID NO: 6) | RPFGNAMDI (SEQ ID NO: 8) |
| II | GYTFTSYAMH (SEQ ID NO: 5) | YINPYNRGTKYNENFKG (SEQ ID NO: 7) | RPFGNAMDI (SEQ ID NO: 8) |

EXAMPLE 2

Binding Kinetics, Affinity, and Specificity of Anti-BMP6 Antibodies

The binding kinetics, affinity, and selectivity to human BMP-6, as well as human BMP-5 and human BMP-7, for antibodies, or antigen-binding fragments thereof, of the present invention, may be determined by use of a surface plasmon resonance (SPR) biosensor such as a BIAcore® 2000, BIAcore® 3000, or a BIAcore® T100 (GE HealthCare) according to methods known in the art.

Human BMP-5, human BMP-6, human BMP-7, and MAB507 may be purchased from R&D Systems (Minneapolis, Minn.). MAB507 is a commercial antibody that is purported to be specific for BMP-6. Cynomolgus monkey BMP-6 and rat BMP-6 may be made using standard procedures Immobilization of ligands on a CM4 chip (BIAcore #BR-1005-34) may be prepared using EDC/NHS amine coupling method (BIAcore #BR-1000-50). Briefly, the surfaces of all four flow cells may be activated by injecting a 1:1 mixture of EDC/NHS for 7 minutes at 10 μL/minute. Human BMP-5, BMP-6, and BMP-7 may be diluted to 1-2 μg/mL in 10 mM acetate buffer, pH 4.5, and immobilized for approximately 200 resonance units (RU) onto flow cell (Fc) 2, 3 or 4 at a flow rate of 10 μL/minute. Fc1 may be left blank. Unreacted sites may be blocked with a 7 minute injection of ethanolamine at 10 μL/minute. Injections of 3×30 sec of glycine pH 1.5 at 30 μL/minute may be used to remove any non-covalently associated protein. All measurements may be performed at 25 and 37° C. Running buffer may be HBS-EP+ (BIAcore #BR-1006-69). BIAcore T100 Evaluation Software Version 2.0.3 may be used for the analysis.

To determine specificity of Antibody I and MAB 507 between different BMP family members, the antibodies may be prepared at final concentration of 1000, 100, 10, 1, 0.1, 0.01, 0.001, and 0 (blank) nM into the running buffer HBS-EP+. Each cycle may consist of an injection of diluted antibody at 50 μL/minute for 300 seconds over all flow cells, followed by dissociation at 50 μL/minute for 1200 seconds. The chip surface may be regenerated by injecting 10 mM glycine pH 1.5 for 60 seconds at 50 μL/minute and HBS-EP buffer for 30 seconds at 30 μL/minute. Reference-subtracted data may be collected, and the on-rate ($k_{on}$) and off-rate ($k_{off}$) for each ligand may be evaluated using a 1:1 binding model in the BIAevaluation analysis software. The affinity ($K_D$) may be calculated from the binding kinetics according to the relationship $K_D=k_{off}/k_{on}$.

In experiments performed essentially as described in this Example 2, Antibody I binds to human BMP-6 with 0.020 nM affinity. With no detectable binding to human BMP-5 and human BMP-7 at 37° C., Antibody I shows selectivity over the two members of the BMP family that are closest in sequence homology to BMP-6.

The R&D antibody MAB507 binds human BMP-6 with 1 nM affinity, and unlike Antibody I, MAB507 has an affinity of 23 nM towards human BMP-7 (Table 2). MAB507 has no detectable binding to human BMP-5 at 37° C. (Table 2).

Fabs of Antibody I and Antibody II bind to human BMP-6 with similar affinities ranging from 0.08-0.09 nM at 37° C. (Table 3). The Fab of MAB507, Fab507, binds to human BMP-6 with an affinity of 12.2 nM at 37° C. (Table 3).

Antibody I and II Fabs exhibit a 135-150-fold higher affinity toward human BMP-6 than the Fab of MAB507. Antibody I exhibits a 50-fold higher affinity to human BMP-6 when comparing to MAB507.

The Fab of Antibody I binds to human, cynomolgus monkey, and rat BMP-6 with similar affinities ranging from 79.6 to 88.0 pM at 37° C. (Table 4). The high affinity of Antibody I toward cynomolgus monkey BMP-6 and rat BMP-6 allows Antibody I to be used directly in cynomolgus monkey and rat animal models without the need to resort to a surrogate antibody.

TABLE 2

Selectivity of Antibody I and MAB507 Measured by Using SPR

| mAb | Ligands | On Rate ($K_{on}$, $M^{-1}S^{-1}$) | Off Rate ($K_{off}$, $S^{-1}$) | Affinity ($K_D$, nM) | Temperature (° C.) |
|---|---|---|---|---|---|
| Antibody I | Human BMP-5 | | No binding | | 37 |
| | Human BMP-6 | $1.73 \times 10^6$ | $4.05 \times 10^{-5}$ | 0.02 | |
| | Human BMP-7 | | No binding | | |
| MAB507 | Human BMP-5 | | No binding | | 37 |
| | Human BMP-6 | $1.87 \times 10^5$ | $1.87 \times 10^{-4}$ | 1 | |
| | Human BMP-7 | $3.42 \times 10^4$ | $7.93 \times 10^{-4}$ | 23.2 | |

TABLE 3

Binding Kinetics and Affinity of BMP6 Antibodies to Human BMP-6 Measured by Using SPR

| Fab | On Rate ($K_{on}$, $M^{-1}S^{-1}$) | Off Rate ($K_{off}$, $S^{-1}$) | Affinity ($K_D$, nM) | Temperature (° C.) |
|---|---|---|---|---|
| Fab of Antibody I | $2.5 \pm 0.1 \times 10^6$ | $2.3 \pm 0.1 \times 10^{-4}$ | $0.09 \pm 0.01$ | 37 |
| Fab of Antibody II | $3.0 \pm 0.4 \times 10^6$ | $2.5 \pm 0.1 \times 10^{-4}$ | $0.08 \pm 0.01$ | 37 |
| Fab507 | $3.6 \pm 0.7 \times 10^5$ | $4.3 \pm 0.1 \times 10^{-3}$ | $12.2 \pm 2.0$ | 37 |

TABLE 4

Binding Kinetics and Affinity of Antibody I to Human, Cynomolgus Monkey, and Rat BMP-6 Measured by Using SPR

| Fab | BMP-6 Ligands | On Rate ($K_{on}$, $M^{-1}S^{-1}$) (±SD) | Off Rate ($K_{off}$, $S^{-1}$) (±SD) | Affinity ($K_D$, pM) (±SD) | Temperature (°C.) |
|---|---|---|---|---|---|
| Fab of Antibody I | Human | $3.7 \pm 1.5 \times 10^6$ | $2.8 \pm 0.3 \times 10^{-4}$ | $84.5 \pm 24.9$ | 37 |
| | Cyno Monkey | $4.1 \pm 2.2 \times 10^6$ | $2.8 \pm 0.5 \times 10^{-4}$ | $79.6 \pm 29.9$ | |
| | Rat | $4.1 \pm 2.3 \times 10^6$ | $3.0 \pm 0.7 \times 10^{-4}$ | $88.0 \pm 33.1$ | |

EXAMPLE 3

Anti-BMP6 Antibodies Inhibit BMP-6 Induction of Hepcidin Expression

The in vitro cell-based inhibition of human BMP-6 by an antibody, or antigen-binding fragment thereof, of the present invention may be measured in a cell-based assay where BMP-6 induces hepcidin expression. The in vitro cell-based assay may also be used to evaluate the selectivity of BMP-6 antibodies against induction of hepcidin by other BMPs, such as BMP-2, BMP-4, BMP-5, BMP-7, BMP-9, and BMP-10. In the aforementioned in vitro cell-based assay, the binding of BMP ligands to the BMP responsive elements on the hepcidin promoter induces luciferase reporter activity in HepProm_Luc cells. The assay is extremely sensitive, and as such is not appropriate for showing which BMP family members are involved in iron homeostasis. The assay is effective, although, for showing the selectivity of inhibitors against different BMP family members in a cell environment.

The HepProm_Luc cell line may be generated by stable transfection of Hep3B2.1-7 cells (ATCC, Manassas, Va., #HB-8064) with a luciferase reporter vector, containing a cloned hepcidin promoter DNA sequence (HepProm 0.3+1.0 kb). HepProm_Luc cells may be maintained in complete medium of DMEM/high glucose (Hyclone, Logan, Utah, #SH30243.01) plus 5% heat inactivated FBS (Invitrogen, Grand Island, N.Y., #10082-147) with 1× MEM NEAA (Invitrogen, Carlsbad, Calif.) and 200 µg/ml G418 Sulfate (Invitrogen, Grand Island, N.Y., #30-234-CI).

For the assay, HepProm_Luc cells may be resuspended to 150,000 cells/mL in complete medium containing no antibiotic. 0.1 mL of the resuspended HepProm_Luc cells may be added to 96-well microtiter plates (Corning, Lowell, Mass., #3917) at 15,000 cells/well, and the cells may then be incubated for 24 hours at 37° C. under 5% (v/v) $CO_2$. The culture medium may then be removed and the cells starved in 80 µL of OptiMEM I (Invitrogen, Grand Island, N.Y., #31985) with 0.1% (w/v) BSA (Invitrogen, Grand Island, N.Y., #15260) for 5 hours at 37° C. under 5% (v/v) $CO_2$.

10 µL of BMP6 antibodies (10× the final concentration) in OptiMEM I with 0.1% (w/v) BSA may be added to the cells for a final dosage range of 0.2 nM to 20 nM for BMP-6 induction; final dosage range of 7.8 nM to 1000 nM for BMP-5 and BMP-7 induction, and up to 1000 nM, single point dose for BMP-2, BMP-4, BMP-9 and BMP-10 induction. 10 µL of BMP ligand (10× final concentration) may then be added for a final concentration of BMP-2 (3.8 nM), BMP-4 (3.8 nM), BMP-5 (12.8 nM), BMP-6 (3.4 nM), BMP-7 (3.2 nM), BMP-9 (0.8 nM) or BMP-10 (4.1 nM) in each well; the cells may be incubated for 22-24 hours at 37° C. under 5% (v/v) $CO_2$. The culture medium may be removed from the cells, and 50 µL of Glo Lysis Buffer (Promega, Madison, Wis., #E2661) may be added to the cells and incubated at room temperature for 5 minutes after 2 minutes of shaking. 50 µL of Bright Glo™ Luciferase Reagent (Promega, Madison, Wis., #E2620) may then be added to the cells and incubated at room temperature for 5 minutes after 30 seconds of shaking. Luminescence may be measured for 1 sec/well on a Wallac Victor instrument.

For calculating the percentage of inhibition by the BMP-6 antibody, 0% inhibition may be set at the average luminescence for BMP ligand treatment without BMP-6 antibody addition, and 100% inhibition may be set at the average luminescence of no BMP ligand treatment without BMP-6 antibody addition. Three or four parameter curve fit analysis may be performed using GraphPad Prism software (San Diego, Calif.).

In experiments performed essentially as described in this Example 3, Antibodies I and II potently inhibit BMP-6-induced hepcidin promoter luciferase activity of HepProm_Luc cells (Table 5); this inhibition is approximately 22-fold more potent than MAB507.

The data in Table 6 shows that Antibodies I and II do not inhibit BMP-2, BMP-4, BMP-5, BMP-7, BMP-9 and BMP-10 induction of hepcidin promoter luciferase activity significantly when tested at a single point concentration of 1000 nM compared to human IgGPAA4 control. Antibodies I and II in this assay show selectivity over the panel of BMPs tested. MAB507, however, does not show selectivity for BMP-6, and has a mean of 54.2% inhibition at 1000 nM (N=2) against BMP-7 compared to human IgGPAA4 control which has a mean of −1.7% inhibition at 1000 nM (N=6).

TABLE 5

$IC_{50}$ of BMP-6 antibodies in BMP-6 induced Hep_Luc Assay

| Antibody | N | Geometric Mean IC50 (nM) |
|---|---|---|
| I | 5 | 0.99 |
| II | 4 | 0.94 |
| MAB507 | 5 | 22.08 |

TABLE 6

Selectivity of BMP-6 antibodies tested at 1000 nM in BMP-2, BMP-4, BMP-5, BMP-7, BMP-9, BMP-10 induced Hep_Luc Assay

| BMP ligand | Antibody | N | Mean % Inh at 1000 nM | Stdev |
|---|---|---|---|---|
| BMP2 | I | 4 | 8.5 | 14.1 |
| | II | 3 | 6.6 | 5.1 |
| | MAB507 | 3 | −50.6 | 40.5 |
| | Control | 6 | 7.8 | 10.5 |

TABLE 6-continued

Selectivity of BMP-6 antibodies tested at 1000 nM in BMP-2, BMP-4, BMP-5, BMP-7, BMP-9, BMP-10 induced Hep_Luc Assay

| BMP ligand | Antibody | N | Mean % Inh at 1000 nM | Stdev |
|---|---|---|---|---|
| BMP4 | I | 4 | 0.3 | 9.0 |
|  | II | 3 | −2.8 | 6.9 |
|  | MAB507 | 3 | −65.4 | 52.7 |
|  | Control | 6 | 4.2 | 7.9 |
| BMP5 | I | 4 | 3.9 | 8.8 |
|  | II | 3 | 1.9 | 9.3 |
|  | MAB507 | 3 | −43.5 | 34.8 |
|  | Control | 5 | 2.5 | 6.7 |
| BMP7 | I | 4 | −12.0 | 28.1 |
|  | II | 3 | −8.2 | 18.0 |
|  | MAB507 | 2 | 54.2 | 0.8 |
|  | Control | 6 | −1.7 | 11.5 |
| BMP9 | I | 4 | −1.7 | 5.5 |
|  | II | 3 | −2.7 | 6.6 |
|  | MAB507 | 3 | −76.1 | 47.8 |
|  | Control | 6 | 2.8 | 8.7 |
| BMP10 | I | 4 | −6.7 | 6.9 |
|  | II | 3 | 0.9 | 10.8 |
|  | MAB507 | 3 | −87.2 | 80.1 |
|  | Control | 6 | 5.4 | 9.4 |

EXAMPLE 4

Pharmacokinetic/Pharmacodynamic Studies of BMP-6 Antibodies Following a Single Intravenous Dose to Male Cynomolgus Monkeys The serum pharmacokinetics/pharmacodynamics (PK/PD) of an antibody, or antigen-binding fragment thereof, of the present invention may be tested following single intravenous doses to normal male cynomolgus monkeys. Male cynomolgus monkeys may be injected with a single intravenous (IV) bolus dose of antibody in a dose volume of 1 mL/kg. From serum samples taken at different time points, the serum iron concentration, the BMP-6 antibody level, and hepcidin level may be measured.

For pharmacokinetics, serum hepcidin, and BMP-6 quantification, approximately 1.5 mL blood may be collected at time points from each animal in tubes without anticoagulant. The samples may be allowed to clot under ambient conditions prior to centrifugation to obtain serum; samples may be maintained on wet ice prior to storage at approximately −70° C. For clinical pathology analysis, approximately 0.5 mL blood may be collected at time points from each animal via a femoral vein into tubes containing no anticoagulant. The blood may be used to measure serum iron, unsaturated iron binding capacity, total iron binding capacity, percent iron saturation, and standard hematology measurements using standard methods. Hepcidin concentration may be measured as described in Murphy et al., Blood, 110(3):1048 (2007).

Serum samples may be analyzed for concentrations of BMP-6 antibody using a total human IgG ELISA. BMP-6 antibody in serum may be bound to anti-human kappa light chain antibody coated wells of a 96 well microtiter plate (Nunc Immobilizer Amino Cat. #436006) and detected with anti-human IgG4-HRP conjugate antibody (Southern Biotech, #9200-05). The upper and lower limits of detection in the assay may be 200 and 10 ng/mL, respectively. The concentration of immunoreactive BMP-6 antibody may be determined from standard curves prepared from known amounts of the compound in rat serum using a 4/5-parameter algorithm (StatLIA, version 3.2). Pharmacokinetic parameters may be calculated using Watson (Version 7.4 Bioanalytical LIMS) software package (Thermo Scientific). The parameters calculated may include the area under the curve ($AUC_{0-\infty}$), apparent clearance (Cl), and elimination half-life.

In an experiment performed essentially as described in this Example 4, Study I has doses of 0.3, 1.0, 3.0, and 10 mg/kg of Antibody I administered as a single intravenous bolus. Control human IgG4 is dosed at 10 mg/kg. The vehicle in Study I is phosphate buffered-saline (pH 7.4). Data for the pharmacokinetics, serum iron and serum hepcidin responses after administration of Antibody I are measured from each animal pre-dose (day −1) and at 1, 6, 12, 24, 48, 72, 120, 168, 240, 336, 432, 528, and 672 hours post-dose and on study days 36, 43, 50, and 57 for pharmacokinetics, serum hepcidin, and BMP-6 quantification.

In an experiment performed essentially as described in this Example 4, Study II has doses of 0.05, 0.3, and 3.0 mg/kg of Antibody I administered as a single intravenous bolus. Control human IgG4 was dosed at 3 mg/kg. The vehicle in Study II is phosphate buffered-saline (pH 7.4) plus 0.02% Tween80. Data for the pharmacokinetics, serum iron and serum hepcidin responses after administration of Antibody I are measured from each animal pre-dose (day −1) and at 1, 6, 12, 24, 48, 72, 120, 168, 240, 336, 432, 528, 672, 840, 1008, 1176, 1344, 1512, 1680, and 1848 hours post-dose.

In Studies I and II, the maximal serum concentrations ($C_{max}$) of Antibody I increases in an approximately dose proportional fashion over the 0.05- to 10-mg/kg examined. Over the dose range examined, Antibody I displays nonlinear pharmacokinetics with clearance decreasing and elimination half-life increasing with increasing dose. The clearance decreases from ~0.57 to ~0.17 mL/hr/kg over the dose range examined. Over the time frame and dose range studied, the half-life ranges from ~58 to ~295 hours.

Pharmacodynamic data in Tables 8 and 9 show that administration of Antibody I is associated with an initial immediate increase in serum iron that peaks at 24 hours before returning to near-baseline (pre-dose) levels at 120-240 hours after dosing. In the 3 and 10 mg/kg dose groups, serum iron elevates again after 240 hours in a more dose-dependent fashion; prolonged serum iron elevation to the end of the study is observed.

Antibody I administration is also associated with an acute decrease in cynomolgus serum hepcidin that occurs as early as 6 to 12 hours post dose. Serum hepcidin returns to baseline in a dose dependent fashion in Study II, but this dose dependency of hepcidin return to baseline is not as apparent in Study I. The human IgG4 control antibody in Study I shows a decrease in serum hepcidin that is not replicated in Study II. Both studies also show significant changes in serum iron levels in the presence of Antibody I that does not correlate with low observed serum hepcidin levels.

TABLE 8

Study I

Mean serum iron concentrations, ug/dL (2 subjects)

| Sample | Control | Antibody I | | | | | | | |
|---|---|---|---|---|---|---|---|---|---|
| Dose | 10 mg/kg | | 0.3 mg/kg | 1.0 mg/kg | | 3.0 mg/kg | | 10 mg/kg | |
| Time, h | μg/dL | SD | μg/dL | SD | μg/dL | SD | μg/dL | SD | μg/dL | SD |
| 0 | 103 | 15.6 | 119.5 | 16.3 | 93 | 8.5 | 126 | 26.9 | 112 | 12.7 |
| 1 | 97 | 0 | 130 | 9.9 | 86.5 | 10.6 | 110 | 8.5 | 114.5 | 7.8 |
| 6 | 81 | 15.6 | 111.5 | 21.9 | 87 | 14.1 | 96.5 | 2.1 | 95.5 | 20.5 |
| 12 | 135.5 | 6.4 | 189.5 | 19.1 | 176 | 45.3 | 217 | 49.5 | 181.5 | 20.5 |
| 24 | 70.5 | 10.6 | 290 | 2.8 | 221 | 83.4 | 296 | 52.3 | 230.5 | 62.9 |
| 48 | 87 | 2.8 | 257 | 49.5 | 200 | 62.2 | 266 | 12.7 | 257.5 | 14.8 |
| 72 | 77 | 14.1 | 153.5 | 19.1 | 120.5 | 47.4 | 156 | 33.9 | 207 | 73.5 |
| 120 | 61.5 | 12 | 118.5 | 10.6 | 118 | 36.8 | 133.5 | 31.8 | 142 | 9.9 |
| 168 | 75.5 | 7.8 | 155 | 22.6 | 80 | 11.3 | 206.5 | 3.5 | 200 | 45.3 |
| 240 | 67 | 15.6 | 123.5 | 12 | 103 | 35.4 | 155 | 43.8 | 137.5 | 0.7 |
| 336 | 65.5 | 0.7 | 133.5 | 26.2 | 102.5 | 17.7 | 168.5 | 20.5 | 222 | 41 |
| 432 | 58 | 1.4 | 141.5 | 16.3 | 104.5 | 23.3 | 224 | 52.3 | 204.5 | 29 |
| 528 | 62.5 | 3.5 | 163.5 | 21.9 | 145 | 14.1 | 265 | 22.6 | 239.5 | 12 |
| 672 | 83.5 | 6.4 | 110.5 | 3.5 | 99.5 | 31.8 | 184 | 39.6 | 193.5 | 24.7 |
| 864 | 82 | 12.7 | 115 | 12.7 | 92 | 5.7 | 193.5 | 37.5 | 187 | 17 |
| 1032 | 75 | 9.9 | 99 | 32.5 | 75 | 2.8 | 136 | 1.4 | 173.5 | 48.8 |
| 1200 | 84 | 7.1 | 114 | 18.4 | 84.5 | 9.2 | 179.5 | 6.4 | 185 | 14.1 |
| 1368 | 86 | 7.1 | 117 | 1.4 | 76 | 11.3 | 158.5 | 4.9 | 198 | 18.4 |

TABLE 9

Study II

Mean serum iron concentrations, ug/dL (3 subjects for Antibody I)

| Sample | Control | Antibody I | | | | | |
|---|---|---|---|---|---|---|---|
| Dose | 3 mg/kg | | 0.05 mg/kg | | 0.3 mg/kg | | 3.0 mg/kg |
| Time, h | μg/dL | SD | μg/dL | SD | μg/dL | SD | μg/dL | SD |
| 0 | 120.5 | 3.5 | 137.7 | 30.5 | 149.3 | 23.4 | 96.3 | 10.7 |
| 1 | 119 | 28.3 | 152.3 | 34.8 | 121.3 | 31 | 95.3 | 13.6 |
| 6 | 91 | 14.1 | 134.7 | 13.3 | 115 | 32 | 79.7 | 14.6 |
| 12 | 121 | 5.7 | 193 | 37.4 | 201 | 37.3 | 147.3 | 7.6 |
| 24 | 128.5 | 2.1 | 276.3 | 27.5 | 305 | 45.6 | 283.7 | 7.5 |
| 48 | 118.5 | 9.2 | 182.7 | 52.2 | 275.7 | 54.4 | 263.3 | 32 |
| 72 | 85.5 | 0.7 | 165.7 | 56.5 | 192.7 | 36.1 | 163.7 | 45.3 |
| 120 | 81.5 | 3.5 | 149 | 61 | 168 | 32.8 | 153.3 | 13.9 |
| 168 | 96.5 | 9.2 | 138.7 | 38.6 | 189.3 | 22.6 | 143.3 | 10.1 |
| 240 | 108.5 | 20.5 | 105 | 31.5 | 140.3 | 16.7 | 146.7 | 19.4 |
| 336 | 119.5 | 4.9 | 111.3 | 35.4 | 170 | 24.6 | 159 | 80.3 |
| 432 | 96.5 | 4.9 | 179.3 | 40.5 | 249.7 | 24 | 235.7 | 47.4 |
| 528 | 83 | 28.3 | 109.3 | 30.4 | 152.7 | 32.6 | 176.3 | 60.1 |
| 672 | 151 | 15.6 | 125 | 27.9 | 118 | 21 | 184.7 | 25.1 |
| 840 | 106.5 | 37.5 | 134 | 44.8 | 114 | 20 | 161 | 8.5 |
| 1008 | 106.5 | 23.3 | 132 | 32.1 | 126 | 28.8 | 188.7 | 50.6 |
| 1176 | 117.5 | 0.7 | 133.7 | 35.2 | 125.3 | 20.6 | 199.3 | 69.5 |
| 1344 | 111 | 14.1 | 121.3 | 24.4 | 108.7 | 10.5 | 166.7 | 11.6 |
| 1512 | 139.5 | 3.5 | 137.3 | 40.1 | 118.7 | 13.1 | 121.7 | 11.8 |
| 1680 | 141 | 9.9 | 135.7 | 25.1 | 123.7 | 11.4 | 125.7 | 16.4 |
| 1848 | 142 | 11.3 | 141.3 | 43 | 132.7 | 14.6 | 107 | 19.3 |

Pharmacokinetic/Pharmacodynamic Studies of HuA507 Following a Single Intravenous Dose to Male Cynomolgus Monkeys In an experiment performed essentially as described in this Example 4, the serum PK/PD of HuA507 is tested following a single intravenous dose to normal male cynomolgus monkeys. HuA507 is a chimeric antibody made by replacing the mouse constant regions of the MAB507 antibody from R&D Systems with a human IgG4PAA backbone. A single intravenous bolus 10 mg/kg dose of HuA507 antibody or control human IgG4 is given in a volume of 1 mL/kg. The vehicle in the study is phosphate buffered-saline (pH 7.4). Blood is collected from each animal pre-dose (Day 1) and at 1, 6, 12, 24, 48, 72, 96, 168, 264, 336, 432, 528, and 624 hours post-dose for analyses. With the 10 mg/kg dose of HuA507 antibody, the mean serum iron concentration increases from approximately 150 μg/ml at pre-dose to approximately 210 μg/ml at 12 hours post-dose, but then falls back to baseline by 48 hours. Unlike the prolonged pharmacodynamic effect for Antibody I shown in this Example 4, treatment with HuA507 only shows a short, initial increase in serum iron concentration out to 48 hours, but not the prolonged response seen with Antibody I.

EXAMPLE 5

Efficacy in Rat ACD Model

The efficacy of antibodies, or antigen-binding fragments thereof, of the present invention can be measured in a rat ACD model. In female Lewis rats, 8 to 10 weeks old, inflammation may be induced by one intraperitoneal dose of 5 mg/kg of gram-positive bacterial cell wall extract (Lee Labs, #PG-PS 10S) at day 0. Without any further treatment, reduced hemoglobin concentrations may be seen in this model within 10 days of treatment with the cell wall extract. Treatment with 10 mg/kg of an antibody of the present invention may be started with an IV dose at day 8 and continued weekly IV doses of the antibody. Hemoglobin, serum iron, and hepcidin concentrations may be measured and compared to the values seen with treatment by a HuIgG4 control.

For clinical pathology analysis, approximately 0.2 mL blood may be collected at time points from each animal via a tail clip into tubes containing EDTA. The blood may be used to measure serum iron, unsaturated iron binding capacity, total iron binding capacity, percent iron saturation, and standard hematology measurements using standard methods. For all other analysis, approximately 0.75 mL blood may be collected at time points from each animal via a tail clip into tubes containing no anti-coagulant.

In an experiment performed essentially as described in this Example 5, Antibody I shows a prolonged pharmacodynamic response with statistically significant higher hemoglobin and iron than the hIgG4 isotype control on most days to the end of the study at day 60. Compared to the control, the hemoglobin concentration increase is approximately 0.82-1.5 g/dL. Erythrocytes in the treated group become less microcytic and less hypochromic once Antibody I treatment is initiated. Based on the change in erythrocyte characteristics, the increase in hemoglobin observed in the study can be concluded to derive from increased normalization of erythrocyte size and cellular hemoglobin level rather than increased production of red cells.

We claim:

1. A DNA molecule, comprising a polynucleotide sequence encoding a heavy chain polypeptide having the amino acid sequence of SEQ ID NO: 13.

2. A DNA molecule, comprising a polynucleotide sequence encoding a light chain polypeptide having the amino acid sequence of SEQ ID NO: 12.

3. A DNA molecule, comprising a polynucleotide sequence encoding a heavy chain polypeptide having the amino acid sequence of SEQ ID NO: 13, and comprising a polynucleotide sequence encoding a light chain polypeptide having the amino acid sequence of SEQ ID NO: 12.

4. A mammalian cell, comprising both a polynucleotide encoding a heavy chain polypeptide having the amino acid sequence of SEQ ID NO: 13 and a polynucleotide sequence encoding a light chain polypeptide having the amino acid sequence of SEQ ID NO: 12, wherein the mammalian cell is capable of expressing an antibody comprising a heavy chain having the amino acid sequence of SEQ ID NO: 13, and a light chain having the amino acid sequence of SEQ ID NO: 12.

5. A mammalian cell, comprising the DNA molecule of claim 3, wherein the mammalian cell is capable of expressing an antibody comprising a heavy chain having the amino acid sequence of SEQ ID NO: 13, and a light chain having the amino acid sequence of SEQ ID NO: 12.

6. The mammalian cell of claim 4 or 5, wherein the mammalian cell is selected from the group consisting of CHO cells, NS0 cells, HEK293 cells, or COS cells.

7. A process for producing an antibody comprising a heavy chain whose amino acid sequence is SEQ ID NO: 13 and a light chain whose amino acid sequence is SEQ ID NO: 12, comprising cultivating the mammalian cell of claim 4 under conditions such that the antibody is expressed, and recovering the expressed antibody.

8. A process for producing an antibody comprising a heavy chain whose amino acid sequence is SEQ ID NO: 13 and a light chain whose amino acid sequence is SEQ ID NO: 12, comprising cultivating the mammalian cell of claim 5 under conditions such that the antibody is expressed, and recovering the expressed antibody.

9. An antibody produced by the process of claim 7.

10. An antibody produced by the process of claim 8.

\* \* \* \* \*

UNITED STATES PATENT AND TRADEMARK OFFICE
CERTIFICATE OF CORRECTION

| | | |
|---|---|---|
| PATENT NO. | : 8,980,582 B2 | Page 1 of 1 |
| APPLICATION NO. | : 14/316137 | |
| DATED | : March 17, 2015 | |
| INVENTOR(S) | : Seo et al. | |

It is certified that error appears in the above-identified patent and that said Letters Patent is hereby corrected as shown below:

In the Claims:

At Column 34, Line 60: In Claim 4, before "encoding" insert -- sequence --.

Signed and Sealed this
Second Day of February, 2016

Michelle K. Lee
*Director of the United States Patent and Trademark Office*